United States Patent [19]

Imai

[11] Patent Number: 4,463,212
[45] Date of Patent: Jul. 31, 1984

[54] SELECTIVE OLIGOMERIZATION OF OLEFINS

[75] Inventor: Tamotsu Imai, Mount Prospect, Ill.

[73] Assignee: UOP Inc., Des Plaines, Ill.

[21] Appl. No.: 448,552

[22] Filed: Dec. 10, 1982

[51] Int. Cl.³ ............................................. C07C 2/02
[52] U.S. Cl. ................................. 585/530; 585/525; 585/532
[58] Field of Search ...................... 585/525, 530, 532

[56] References Cited

U.S. PATENT DOCUMENTS

| | | | |
|---|---|---|---|
| 2,381,481 | 8/1945 | Anderson | 260/683.15 |
| 2,945,845 | 7/1960 | Schmerling | 260/93.7 |
| 2,965,686 | 12/1960 | Prill | 260/671 |
| 3,153,634 | 10/1964 | Thomas | 252/429 |
| 3,506,633 | 4/1970 | Matsuura et al. | 260/88.2 |
| 3,660,419 | 5/1972 | Shepherd et al. | 260/309 |
| 3,725,497 | 4/1973 | Arakawa et al. | 260/683.15 D |
| 4,048,108 | 9/1977 | Ryu | 252/442 |
| 4,048,109 | 9/1977 | Ryu | 252/442 |
| 4,083,885 | 4/1978 | Rodewald | 585/465 |

OTHER PUBLICATIONS

*Nature* (London), 158, 94 (1946) A. G. Evans, G. W. Meadows & M. Polyani.

Primary Examiner—Curtis R. Davis
Attorney, Agent, or Firm—James R. Hoatson, Jr.; Raymond H. Nelson; William H. Page, II

[57] ABSTRACT

Olefinic hydrocarbons containing from 2 to about 6 carbon atoms may be oligomerized to provide selective olefins by treatment with a catalyst comprising a metal halide intercalated in a carbon matrix. The oligomerization may be effected at temperatures ranging from about 50° to about 350° C. and a pressure in the range of from about 500 to about 2000 psig in the presence of a catalyst such as antimony fluoride intercalated in graphite.

4 Claims, No Drawings

SELECTIVE OLIGOMERIZATION OF OLEFINS

BACKGROUND OF THE INVENTION

Heretofore, the prior art has disclosed catalysts for the polymerization of olefins, said catalysts comprising those known in the art as Ziegler-Natta catalysts. These catalysts typically consist of titanium tetrachloride which has been activated with an aluminum alkyl and operate in the form of a sludge or slurry. For example, U.S. Pat. No. 2,945,845 discloses a titanium tetrachloride catalyst which is used in conjunction with an organic compound such as triethyl aluminum or U.S. Pat. Nos. 3,660,419 and 3,725,497 which also teach the use of titanium tetrachloride catalysts which have been activated with the organoaluminum compounds. Titanium tetrachloride is reduced to lower valent titanium chloride by the aluminum alkyl. Other titanium halide catalysts which have been disclosed in the prior art include those such as shown in U.S. Pat. No. 3,153,634 in which a titanium tetrahalide is impregnated on an alumina such as gamma-alumina and is thereafter subjected to reducing conditions such as by treatment with hydrogen at temperatures ranging from 250° to 500° C. Alternatively, the impregnated alumina could be reduced by contact with a solution or dispersion of a reducing agent such as the alkali or alkaline earth metals or metal hydrides, etc. However, the catalysts thus prepared are useful in polymerizing olefins to form solid polymers, and specifically, high molecular weight solid polymers in which the molecular weight will range from 300 to 100,000. In addition to describing the preparation of solid polymers, this patent also states that aromatic hydrocarbons such as benzene, toluene, xylene or ethers may be used as suitable diluents. However, this is in contradistinction to the heterogeneous oligomerization catalyst of the type hereinafter set forth in greater detail in which it has been found that it is not possible to utilize aromatic hydrocarbons as diluents inasmuch as the olefinic hydrocarbon, if present, would enter into the reaction in which parts or all of the olefin would act as an alkylating agent rather than as a monomer in a polymerization reaction.

Another patent, namely U.S. Pat. No. 2,965,686, discloses a catalyst which is prepared by activating alumina by evacuation at a temperature of 600° C. for a period ranging from about 18 hours to about 21.5 hours. After activation of the alumina, the base was then treated with a mixture of argon, an inert gas, and titanium tetrachloride vapor at a temperature of about 600° C. for an unspecified period of time. The resultant catalyst was then used in an alkylation reaction for the propylation of cumene to form diisopropylbenzene. This patent is silent as to the type of alumina which was used as the base for the catalyst. In the process of the present invention, as will hereinafter be set forth in greater detail, it is believed that the substrate or base which is utilized must possess surface hydroxyl groups and therefore it is necessary to use specific types of alumina such as gamma-alumina, eta-alumina, etc. Another reference which discloses polymerization catalysts in U.S. Pat. No. 3,506,633 which teaches polymerization catalysts having a chlorine:titanium ratio of 2.5 to 3.5. However, in contradistinction to the catalyst of the present invention, this catalyst is used to prepare solid polymers. Yet another patent in this field is U.S. Pat. No. 2,381,481 in which the preparation and use of a catalyst prepared by treating alumina gel with fluotitanic acid is disclosed. However, as is the case of the previously mentioned patents, this catalyst is used to polymerize olefins to heavier hydrocarbons, i.e. solid polymers, and is also used to alkylate paraffins with olefins, usually at temperatures ranging between 700° and 900° F. or higher.

It has been known that Lewis acids such as metal halides can catalyze the Friedel Crafts type reactions and since Lewis acids alone show no or only mild catalytic activity, Lewis acids normally require cocatalyst. Titanium tetrahalides are well-known Lewis acids (Reference: A. G. Evans, G. W. Meadows and M. Polyani; *Nature* (London), 158, 94 (1946)).

In addition to these patents, two other U.S. patents also teach a process for oligomerizing olefinic compounds. U.S. Pat. No. 4,108,920 utilizes, as a catalyst for the reaction, a compound which has been prepared by heating a metal oxide which possesses surface hydroxyl groups with hydrogen and nitrogen at an elevated temperature which may range from about 350° C. to about 550° C. and thereafter impregnating the heated metal oxide with a solution of titanium tetrafluoride. The impregnated oxide is then cold-rolled, followed by steam drying and further drying the component at an elevated temperature of from about 200° to about 600° C. in an inert atmosphere. Likewise, U.S. Pat. No. 4,110,410 also discloses a process for the oligomerization of olefins using a catalyst which has been prepared by heating a metal oxide again possessing surface hydroxyl groups at a temperature in the range of from about 400° to about 600° C., contacting the metal oxide with a titanium tetrachloride vapor in a series of steps at progressively higher temperatures whereby the titanium tetrachloride is composited on the metal oxide. The impregnated metal oxide is then heated in contact with hydrogen at elevated temperatures ranging from about 300° to about 700° C. to reduce the titanium to a valence state of less than +4 and thereafter using this catalyst to oligomerize olefins. U.S. Pat. Nos. 4,048,108 and 4,048,109 disclose methods for preparing the catalysts which are utilized in the aforementioned two U.S. patents. However, the process using these catalysts results in a product mix which is heavy in highly branched chain products. As will hereinafter be shown in greater detail, by utilizing the catalysts of the present invention, it is possible to obtain selective oligomers of olefinic hydrocarbons, the oligomers being selectively less branched compounds.

SUMMARY OF THE INVENTION

This invention relates to a process for the oligomerization of olefinic hydrocarbons. More specifically, the invention is concerned with a process for the oligomerization of olefinic hydrocarbons utilizing a specific catalyst composition to obtain selective oligomers of the olefinic feedstock.

Many olefinic hydrocarbons which contain from 4 to about 12 carbon atoms in the chain are utilized in various industries in many ways. For example, one specific use of these hydrocarbons and especially hydrocarbons containing 8 carbon atoms in the chain, is as a component in motor fuels, such as internal combustion engines utilizing gasoline or engines using diesel fuel. The presence of these compounds in motor fuels will improve the octane number of the fuel to a higher level, thus enabling the motor fuel such as gasoline to produce a relatively higher octane number, either in the leaded or unleaded state. Another use of such compounds would be as plasticizers, especially those olefins which possess a relatively straight chain configuration with a minimum of branching such as 1 or 2 methyl substituents on the chain. These compounds will find use, as hereinbefore set forth, as plasticizers which, when added to a plastic will facilitate compounding and improve the flexibility and other properties of the finished product. Examples of uses for olefins containing 6 carbon atoms would be in the synthesis of flavors, perfumes, medicines, dyes and resins, while olefins containing 12 carbon atoms may be used as intermediates in the preparation of detergents, lubricants, additives, plasticizers, in the synthesis of flavors, perfumes, medicines, oils, dyes, etc.

It is therefore an object of this invention to provide a process for the oligomerization of olefinic hydrocarbons.

A further object of this invention is to provide a process for the oligomerization of olefinic hydrocarbons utilizing a specific catalyst system whereby selective oligomers may be obtained thereby.

In one aspect, an embodiment of this invention resides in a process for the selective oligomerization of an olefinic hydrocarbon which comprises treating said olefinic hydrocarbon at oligomerization conditions in the presence of a catalyst composite comprising a metal halide intercalated in a carbon matrix, and recovering the resultant selective oligomer.

A specific embodiment of this invention is found in a process for the oligomerization of butene-2 which comprises oligomerizing said butene-2 at a temperature in the range of from about 50° to about 350° C. and a pressure in the range of from about 50 to about 2000 psig in the presence of a catalyst comprising antimony pentafluoride-graphite intercalated, and recovering the selective oligomers comprising methyl heptene, dimethyl hexene, and tripentene.

Other objects and embodiments can be found in the following further detailed description of the present invention.

DETAILED DESCRIPTION OF THE INVENTION

As hereinbefore set forth, the present invention is concerned with a process for the oligomerization of olefinic hydrocarbons containing from about 2 to about 6 carbon atoms, said oligomerization being effected in the presence of a catalyst of the type hereinafter set forth in greater detail to obtain selective oligomers. The term "polymerization" has a relatively broad meaning in the chemical art. Although it is generally referred to as the preparation of relatively high molecular weight polymers, it may also refer to low molecular weight polymers. In contradistinction to this, the term "oligomerization" refers to polymeric compounds in which the molecules consist of only a relatively few monomer units and would include dimerization, trimerization or tetramerization. In view of the unpredictable art of catalysis, it was totally unexpected that by utilizing the catalytic composition of matter of the present invention, it would be possible to obtain selective oligomers which possess a minimum amount of branching. This result was even more unexpected in view of prior art patents such as those previously described utilizing titanium flouride as a catalyst which produced oligomers possessing a relatively high degree of branching. Therefore, the process of this invention, utilizing a type of catalyst hereinafter described, contrasts with the process hereinbefore described, inasmuch as the catalyst of the present invention possesses different capabilities and functions in performing its catalytic duty. Olefinic hydrocarbons which may be used as the feedstock and which may undergo oligomerization according to the process of this invention comprise those olefins containing from about 2 to about 6 carbon atoms such as ethylene, propylene, butene-1, butene-2, pentene-1, pentene-2, hexene-1, hexene-2, hexene-3, etc. It is also contemplated within the scope of this invention that branched chain isomers of these olefins as well as olefins containing more than 6 carbon atoms may also undergo oligomerization, although not necessarily with equivalent results.

The catalyst system which is used to effect the oligomerization of the aforementioned olefins comprises a metal halide intercalated in a carbon matrix. In the preferred embodiment of the invention, the carbon matrix comprises graphite, although it is also contemplated within the scope of this invention that other forms of carbon may be employed, although not necessarily with equivalent results. The metal halides which are intercalated in the carbon matrix will comprise those metal halides which may be considered as Lewis acids, that is, a metal halide which will be a proton donor. For purposes of the present invention, the term "metal" as used in the specification and appended claims will also include those elements which are metalloid in nature such as boron and phosphorus. Examples of metal halides which may be employed will include those halides of metals selected from Groups, IIIA, IVA, VA, IB, IIB, IIIB, IVB, VB, VIB and VIII of the Periodic Table. In the preferred embodiment of the invention, the halogens of the metal halide will be selected from the group consisting of chlorine, bromine and fluorine. Some specific examples of these metal halides which are intercalated on the carbon matrix will include copper chloride, copper bromide, copper fluoride, zinc chloride, zinc bromide, zinc fluoride, cadmium chloride, cadmium bromide cadmium fluoride, silver chloride, silver bromide, silver fluoride, boron chloride, boron bromide, boron fluoride, aluminum chloride, aluminum bromide, aluminum fluoride, gallium chloride, gallium bromide, gallium fluoride, indium chloride, indium bromide, indium fluoride, germanium chloride, germainum bromide, germanium fluoride, tin chloride, tin bromide, tin fluoride, lead chloride, lead bromide, lead fluoride, phosphorus chloride, phosphorus bromide, phosphorus fluoride, antimony chloride, antimony bromide, antimony fluoride, bismuth chloride, bismuth bromide, bismuth fluoride, scandium chloride, scandium bromide, scandium fluoride, yttrium chloride, yttrium bromide, yttrium fluoride, vanadium chloride, vanadium bromide, vanadium fluoride, tantalum chloride, tantalum bromide, tantalum fluoride, chromium chloride, chromium bromide, chromium fluoride, molybdenum chloride, molybdenum bromide, molybdenum fluoride, tungsten chloride, tungsten bromide, tungsten fluoride, iron chloride, iron bromide, iron fluoride, cobalt chloride, cobalt bromide, cobalt fluoride, nickel chloride, nickel bromide, nickel fluoride, etc. Again, in the preferred embodiment of the invention, the metal halides will be present in the intercalate composite in an amount in the range of from about 5% to about 75% by weight of the composite.

The metal halide-carbon intercalate may be prepared in any manner known in the art, a representative example of the process for preparing these composites being to admix the metal halide and the carbon such as graphite in amounts previously predetermined and after thorough mixing, to heat the mixture at a temperature slightly in excess of ambient up to about 150° C. or higher for a predetermined period of time, the duration of the heating period being dependent upon the operating parameters as exemplified by the reaction temperature.

The process of the present invention in which an olefinic hydrocarbon is oligomerized to obtain selective oligomers thereof may be effected in any conventional manner including batch and continuous type operations. When a batch type operation is employed, a quantity of the catalyst is placed in an appropriate apparatus which may comprise a reaction flask, autoclave, etc., the placement of the catalyst in the reaction apparatus being effected while maintaining the catalyst in an inert atmosphere such as nitrogen, helium, argon, etc. Thereafter, the olefinic hydrocarbon which is to be oligomerized is charged to the reaction apparatus containing the catalyst at predetermined reaction conditions which may include a temperature in the range of from about 50° to about 350° C., pressures ranging from about 50 to about 2000 psig, and Liquid Hourly Space Velocities ranging from about 0.5 to about 10. It is also contemplated within the scope of this invention that the olefinic hydrocarbon which is to be oligomerized may be admixed with paraffins which act as diluents for the reaction. Upon completion of the desired reaction period, which may range from about 0.5 up to about 10 hours or more in duration, the reaction mixture, after allowing the apparatus to return to room temperature and atmospheric pressure, is recovered and the desired products, comprising the minimal branched oligomers separated from the catalyst and unreacted olefins by conventional means such as fractional distillation, are recovered.

It is also contemplated within the scope of this invention that the oligomerization reaction may be effected in a continuous manner of operation. When such a type of operation is employed, the halide-alumina catalyst is placed in an appropriate reaction apparatus which is maintained at the proper operating conditions of temperature and pressure. The olefinic feedstock which is to be oligomerized is continuously charged to the reaction vessel, usually in admixture with a paraffinic hydrocarbon which is used as a diluent. After a predetermined period of time in contact with the catalyst, the reactor effluent is continuously discharged and the effluent is subjected to conventional means of separation whereby any unreacted olefins may be recycled to the reaction apparatus to form a portion of the feedstock, while the desired oligomers are recovered. Inasmuch as the catalyst is in solid form, various methods of continuous operation may be employed. For example, the catalyst may be positioned in the reaction apparatus as a fixed bed and the feedstock passed over said catalyst in either an upward or downward flow. Another method of effecting the process is by utilizing a moving bed type of operation in which the catalyst and feedstock are passed through the reaction apparatus either concurrently or countercurrently to each other while effecting contact between the two. The third method of effecting a continuous type of operation comprises the slurry type in which the catalyst is carried into the reactor as a slurry in the liquid feed. Regardless of which type of operation is employed, the reactor effluent is continuously recovered and subjected to separation means whereby the desired minimal branched oligomers are separated and recovered.

Examples of oligomers which may be obtained by utilizing the particular catalyst in the process of the present invention will include n-butene, n-hexene, 4-methyl-1-pentene, 3-methyl-1-pentene, 2-methyl-1-pentene, n-octene, the isomeric methylheptenes, dimethylhexenes, n-decene, the isomeric nonenes, dimethyloctenes, n-dodecene, the isomeric undecenes, dimethyldecenes, etc.

The following examples are given for purposes of illustrating the process of the present invention. However, it is to be understood that these examples are merely illustrative in nature and that the present process is not necessarily limited thereto.

EXAMPLE I

A catalyst comprising 1 gram of an antimony pentafluoride graphite intercalate containing 50% by weight of antimony pentafluoride was placed in an 850 cc rotating autoclave. A charge stock comprising 60 grams of a butene 2/n-butane mixture consisting of 60% by weight of butene-2 and 40% by weight of n-butane was charged to the autoclave. After sealing the autoclave, it was then heated to a temperature of 200° C. and maintained thereat for a period of 6 hours, the maximum pressure during this time reaching 400 psig. At the end of the 6 hour period, heating was discontinued and after the autoclave had reached room temperature, the excess pressure was discharged. The autoclave was opened and the reaction mixture subjected to analysis, it being determined that there had been a 51% conversion of the butene-2 with a 58 wt. % selectivity to $C_8$ olefins. Further analysis determined the isomer distribution of the $C_8$ olefins to be as follows:

| Isomer | Percent |
| --- | --- |
| methylheptene | 1.4 |
| dimethylhexene | 87.6 |
| trimethylpentene | 10.5 |

It is therefore apparent that the dimethylhexene isomer was selectively produced with respect to the other two isomers. In addition, the selectivity to higher olefin oligomers other than $C_8$ olefins was relatively high, thus indicating that the catalyst may be particularly suitable for producing components which are readily useable in jet fuels or diesel fuels.

EXAMPLE II

In a manner similar to that set forth in Example I above, a catalyst comprising aluminum chloride intercalated in graphite may be used in the oligomerization of propylene by treating a mixture of propylene and propane in a wt. ratio of 60% propylene and 40% propane at a temperature of about 200° C. and a pressure of about 500 psi to obtain a mixture of selective oligomers which may comprise n-hexene, methylpentene and dimethylbutene.

EXAMPLE III

In this example, a catalyst composite comprising boron fluoride intercalated in graphite, zirconium tetrachloride intercalated in graphite or gallium bromide intercalated in graphite may be used in a manner similar to that hereinbefore set forth to oligomerize an olefin such as pentene. The particular catalyst composite which is employed may be placed in a rotating autoclave while a charge stock comprising a mixture of pentene-2 and pentane may be charged to the autoclave. The autoclave may then be sealed and heated to a temperature of about 250° C. for a period of about 6 hours while maintaining an operating pressure of 500 psig. At the end of the reaction period, the autoclave may be allowed to return to room temperature and after the excess pressure is discharged, the autoclave may be opened and the reaction mixture recovered therefrom. The process thus effected may result in the production of selective oligomers comprising a mixture of methylnonene, dimethyloctene and trimethylheptene.

I claim as my invention:

1. A process for the selective oligomerization of butene-2 which comprises treating said butene-2 at oligomerization conditions in the presence of a catalyst composite comprising antimony pentafluoride intercalated in a carbon matrix, and recovering the resultant selective oligomer.

2. The process as set forth in claim 1 in which said oligomerization conditions include a temperature in the range of from about 50° to about 350° C. and a pressure in the range of from about 50 to about 2000 pounds per square inch gauge.

3. The process as set forth in claim 1 in which said antimony pentafluoride is present is said matrix in an amount in the range of from about 5% to about 75% by weight of said composite.

4. The process as set forth in claim 1 in which the carbon in said matrix is in the form of graphite.

* * * * *